(12) United States Patent
Ella et al.

(10) Patent No.: US 9,901,675 B2
(45) Date of Patent: Feb. 27, 2018

(54) INFUSION SET INSERTION DEVICE AND METHOD OF USE

(71) Applicant: MEDTRONIC MINIMED, INC., Northridge, CA (US)

(72) Inventors: Ella Isabella F. Ella, Chino Hills, CA (US); Ulrich H. Rankers, Porter Ranch, CA (US); Risako Morawiec, Santa Monica, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 219 days.

(21) Appl. No.: 14/553,528

(22) Filed: Nov. 25, 2014

(65) Prior Publication Data

US 2016/0144106 A1 May 26, 2016

(51) Int. Cl.
*A61M 5/158* (2006.01)
*A61B 5/00* (2006.01)

(52) U.S. Cl.
CPC ........... *A61M 5/158* (2013.01); *A61B 5/6849* (2013.01); *A61M 2005/1585* (2013.01)

(58) Field of Classification Search
CPC .. A61M 2005/1585; A61M 2005/1583; A61M 5/3287; A61B 5/6848; A61B 5/6849
See application file for complete search history.

(56) References Cited

U.S. PATENT DOCUMENTS

| | | | |
|---|---|---|---|
| 4,755,173 A | 7/1988 | Konopka et al. | |
| 5,391,250 A | 2/1995 | Cheney, II et al. | |
| 5,485,408 A | 1/1996 | Blomquist | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,851,197 A * | 12/1998 | Marano ................ | A61M 5/158 604/131 |
| 5,868,711 A * | 2/1999 | Kramer .............. | A61B 17/3472 604/136 |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,186,982 B1 | 2/2001 | Gross et al. | |
| 6,246,992 B1 | 6/2001 | Brown | |

(Continued)

*Primary Examiner* — Kevin C Sirmons
*Assistant Examiner* — William Carpenter
(74) *Attorney, Agent, or Firm* — Medtronic MiniMed, Inc.

(57) ABSTRACT

An infusion set insertion device and method of use with an insertion device for an infusion set having an infusion set body including: a barrel defining a pull handle cavity; a pull handle slideably disposed in the pull handle cavity, the pull handle having an outer surface and defining an infusion set cavity and a release button cavity, the pull handle having a cocked position and an advanced position relative to the barrel; a release button slideably disposed in the release button cavity, the release button having a loaded position and a released position relative to the pull handle; and a driver operable to move the pull handle from the cocked position to the advanced position; wherein the release button extends a first axial distance beyond the outer surface when in the loaded position and extends a second axial distance into the infusion set cavity when in the released position.

16 Claims, 7 Drawing Sheets

(56) References Cited

U.S. PATENT DOCUMENTS

| | | |
|---|---|---|
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,830,562 B2 * | 12/2004 | Mogensen ............ A61M 5/158 604/136 |
| 7,003,336 B2 | 2/2006 | Holker et al. |
| 7,029,444 B2 | 4/2006 | Shin et al. |
| 7,056,302 B2 * | 6/2006 | Douglas ................ A61M 5/158 604/117 |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,409,145 B2 * | 4/2013 | Raymond ......... A61M 5/14244 604/157 |
| 2003/0158520 A1 * | 8/2003 | Safabash ................ A61M 5/158 604/116 |
| 2004/0143218 A1 * | 7/2004 | Das .................... A61B 17/3417 604/164.06 |
| 2004/0158207 A1 * | 8/2004 | Hunn .................... A61M 5/158 604/164.01 |
| 2005/0101912 A1 * | 5/2005 | Faust .................... A61M 5/158 604/117 |
| 2007/0123819 A1 | 5/2007 | Mernoe et al. |
| 2009/0082728 A1 * | 3/2009 | Bikovsky ............ A61M 5/1413 604/136 |
| 2009/0304812 A1 * | 12/2009 | Staniforth ............ A61K 9/0014 424/618 |
| 2010/0160861 A1 | 6/2010 | Causey, III et al. |

\* cited by examiner

INFUSION SET INSERTION DEVICE AND METHOD OF USE

TECHNICAL FIELD

The technical field of this disclosure is personal medical systems, particularly, infusion set insertion devices and methods of use.

BACKGROUND OF THE INVENTION

Certain medical conditions or diseases require that patients intermittently inject a drug or therapeutic agent subcutaneously to maintain the medical condition or disease under control. Multiple daily injections (MDIs) may be required. One such medical condition is diabetes, for which insulin is injected to regulate blood glucose. An estimated twenty-six million people in the United States, or about 8% of the population, have diabetes. This percentage is expected to increase in the near-term as the population ages.

An infusion set is used with an insulin pump to deliver insulin subcutaneously to the patient in treating many patients for diabetes. The infusion set can include a hollow flexible cannula or a needle attached to an infusion set body, an adhesive patch for securing the infusion set body to the patient, and tubing to deliver insulin from the insulin pump through the cannula or needle and to the patient. The infusion set remains in place on the body for up to two or three days.

Infusion set insertion devices have been developed to assist the patient in deploying the infusion set, i.e., in inserting the cannula or a needle into the skin at the desired infusion site on the body and securing the infusion set to the body with the adhesive patch. An infusion set is loaded into the insertion device, a spring on the insertion device is cocked, the insertion device with the loaded infusion set is positioned over the infusion site, and the spring released, inserting the cannula or a needle into the skin and placing the adhesive patch against the skin.

Unfortunately, present insertion devices employ a pull handle that makes it difficult for the user to properly load the infusion set into the insertion device. The pull handle is used both to cock the spring on the insertion device and to release the insertion device from the infusion set after the spring has been released and the infusion set has been placed at the infusion site. Users prevent the infusion set from seating properly by holding the pull handle in the release position manually or by placing the insertion device on a flat surface such as a table while attempting to load the infusion set into the insertion device. Users can also depress the pull handle into the release position after the infusion set has been properly loaded, dislodging the infusion set from the properly loaded position. The pull handle can be depressed by handling or by placing the pull handle downward on a flat surface such as a table.

It would be desirable to have an infusion set insertion device and method of use that would overcome the above disadvantages.

SUMMARY OF THE INVENTION

One aspect of the invention provides an insertion device for an infusion set having an infusion set body, the insertion device including: a barrel defining a pull handle cavity; a pull handle slideably disposed in the pull handle cavity, the pull handle having an outer surface and defining an infusion set cavity and a release button cavity, the infusion set cavity being sized to receive the infusion set body, the pull handle having a cocked position and an advanced position relative to the barrel; a release button slideably disposed in the release button cavity, the release button having a loaded position and a released position relative to the pull handle; and a driver operable to move the pull handle from the cocked position to the advanced position. The release button extends a first axial distance beyond the outer surface when in the loaded position and extends a second axial distance into the infusion set cavity when in the released position.

Another aspect of the invention provides a method of use for an insertion device with an infusion set having an adhesive patch attachable to a user. The insertion device has a barrel defining a pull handle cavity; a pull handle slideably disposed in the pull handle cavity, the pull handle having an outer surface and defining an infusion set cavity and a release button cavity; and a release button slideably disposed in the release button cavity. The method includes: loading the infusion set into the infusion set cavity until the infusion set contacts the release button, the release button extending a second axial distance into the infusion set cavity; seating the infusion set within the infusion set cavity to extend the release button a first axial distance beyond the outer surface of the pull handle; drawing back the pull handle to a cocked position relative to the barrel; positioning the barrel over an infusion site of the user; triggering the pull handle to move the pull handle from the cocked position to an advanced position; pressing the release button to free the infusion set from the infusion set cavity and fix the adhesive patch to the user.

Another aspect of the invention provides an insertion device for an infusion set having an infusion set body, the insertion device including: a barrel defining a pull handle cavity, the barrel having a pair of radially opposed trigger button openings; a pull handle slideably disposed in the pull handle cavity, the pull handle having an outer surface and defining an infusion set cavity and a release button cavity, the infusion set cavity being sized to receive the infusion set body, the pull handle having a cocked position and an advanced position relative to the barrel; a release button slideably disposed in the release button cavity, the release button having a loaded position and a released position relative to the pull handle; a barrel spring operable to bias the barrel toward the outer surface of the pull handle and operable to move the pull handle from the cocked position to the advanced position; and a pair of radially opposed trigger buttons operably connected to and biased radially outward toward the barrel, one of the pair of radially opposed trigger buttons being engagable with each of the pair of radially opposed trigger button openings, the pair of radially opposed trigger buttons being operable to maintain the pull handle in the cocked position when the radially opposed trigger buttons are engaged with the pair of radially opposed trigger button openings, the pair of radially opposed trigger buttons being operable to release the pull handle from the cocked position when the radially opposed trigger buttons are disengaged from the pair of radially opposed trigger button openings. The release button extends a first axial distance beyond the outer surface when the release button is in the loaded position and the infusion set body is seated in the infusion set cavity; the release button extends a second axial distance into the infusion set cavity when the release button is in the released position to dislodge the infusion set body from the infusion set cavity; and the outer surface of the pull handle is concave and has an axial concavity depth, the axial concavity depth being greater than or equal to the first axial distance.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

Like elements share like reference numbers in the various drawings.

DETAILED DESCRIPTION

Figure 1A:
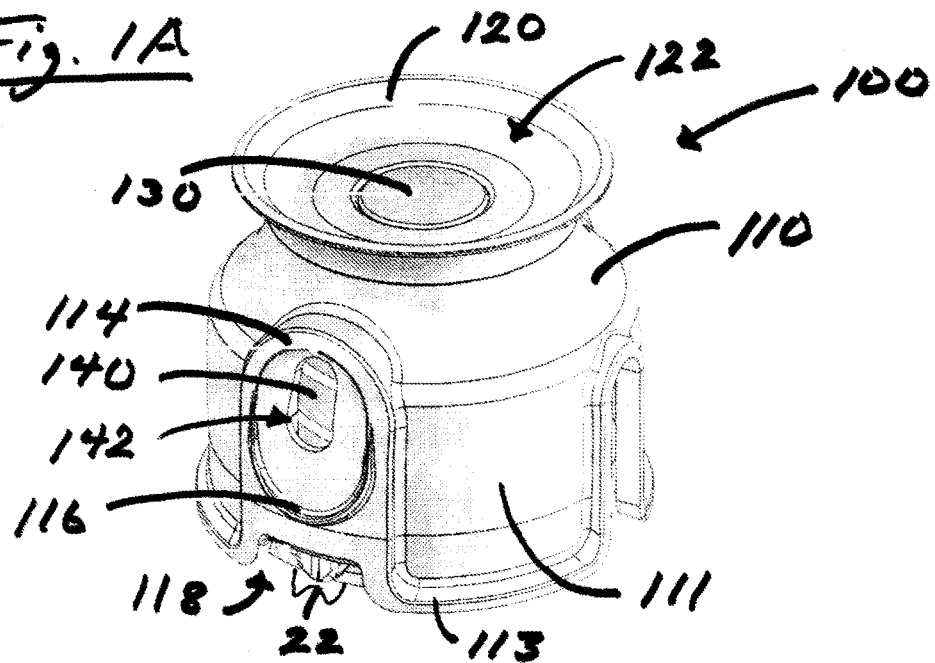
FIGS. 1A-1C are perspective, side, and exploded views, respectively, of one embodiment of an infusion set insertion device made in accordance with the invention.
Figure 1B:
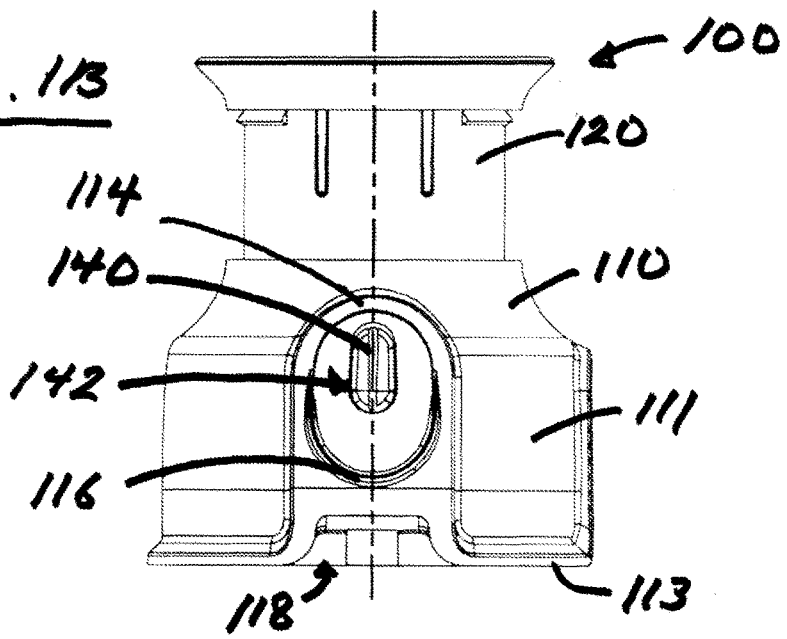
Figure 1C:
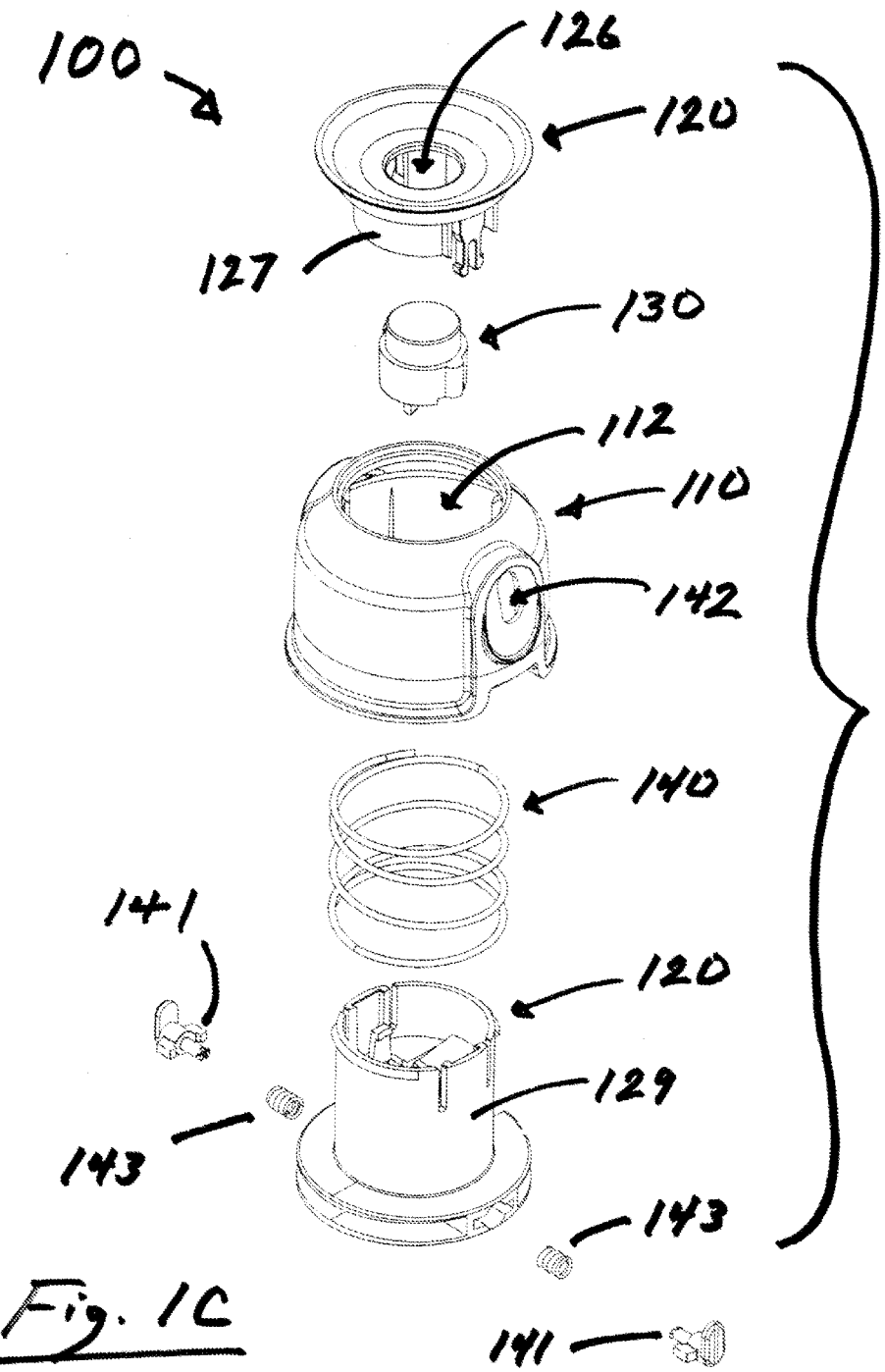

FIGS. 1A-1C, in which like elements share like reference numbers, are perspective, side, and exploded views, respectively, of one embodiment of an infusion set insertion device made in accordance with the invention. The insertion device 100 is operable to deliver an infusion set to the user at an infusion site, inserting the needle of the infusion set subcutaneously.

Referring to FIG. 1A, the release button 130 is in the released position and the pull handle 120 is in the advanced position for the insertion device 100. The insertion device 100 includes a barrel 110, a pull handle 120 slideable within the barrel 110, and a release button 130 slideable within the pull handle 120. The pull handle 120 has an outer surface 122 and includes an infusion set cavity (not shown) into which the infusion set can be loaded. In this example, the outer surface 122 is concave. In this example, the pull handle 120 is triggered from the cocked position to the advanced position by pressing the pair of radially opposed trigger buttons 141 into the pair of radially opposed trigger button openings 142 in the barrel 110. The pair of radially opposed trigger buttons 141 are biased radially outward toward the barrel 110. The pair of radially opposed trigger buttons 141 maintain the pull handle 120 in the cocked position when the radially opposed trigger buttons 141 are engaged with the pair of radially opposed trigger button openings 142. The pair of radially opposed trigger buttons 141 release the pull handle 120 from the cocked position when the radially opposed trigger buttons 141 are disengaged from the pair of radially opposed trigger button openings 142.

The insertion device 100 can include structural elements to make it easier for the user to handle the insertion device 100 and deploy the infusion set. In one example, the barrel 110 has a raised button guard 114 near the trigger button 141. The barrel 110 has an exterior surface 111 defining a raised button guard 114 operable to prevent inadvertent actuation of the trigger button 141 when the pull handle 120 is in the cocked position. Thus, the trigger button 141 is protected and unlikely to be pushed before the barrel 110 is positioned at the infusion site of the user.

In another example, the barrel 110 has an exterior surface 111 defining a finger grip 116 adjacent to the at least one trigger button 141, the finger grip 116 being operable to assist a user in gripping the barrel 110. Those skilled in the art will appreciate that the rich finger grip 116 can have different textures, such as ridges, indentations, protruding dots, or the like, as desired for a particular application. In this example, the finger grip 116 is a ridged finger grip.

In yet another example, the insertion device 100 provides ready access to the removable adhesive liner which is removed from the infusion set before affixing the infusion set to the user. The infusion set can include an adhesive patch attached to the infusion set body, with the adhesive patch having a removable adhesive liner 22. The barrel 110 can have a user contact edge 113 where the barrel 110 contacts the user at the infusion site. The user contact edge 113 can define at least one adhesive liner cutout 118, with the at least one adhesive liner cutout 118 providing lateral access to the removable adhesive liner 22 when the infusion set body is seated within the infusion set cavity. Thus, the user can grab the removable adhesive liner 22 from the side of the insertion device 100 and remove the removable adhesive liner 22 from the adhesive patch when the infusion set body is already seated within the infusion set cavity 124.

Referring to FIG. 1B, the pull handle 120 is in the cocked position. The pull handle 120 is drawn back to the cocked position relative to the barrel 110, so that triggering the pull handle 120 moves the pull handle 120 from the cocked position to the advanced position. In this example, the pull handle 120 is triggered by pressing the pair of radially opposed trigger buttons into the pair of radially opposed trigger button openings 142 in the barrel 110. The triggered pull handle 120 delivers the infusion set to the infusion site, subcutaneously inserting the needle of the infusion set in the user.

Referring to FIG. 1C, the insertion device 100 includes the barrel 110, the pull handle 120 slideable within the barrel 110, and the release button 130 slideable within the pull handle 120. In this example, the pull handle 120 includes a handle portion 127 and a plunger portion 129 which are separate prior to assembly of the insertion device 100 but are connected into a single part (the pull handle 120) when the insertion device 100 is fully assembled. The pull handle 120 defines a release button cavity 126 operable to slideably receive the release button 130. The pull handle 120 also defines an infusion set cavity (not shown) operable to receive the infusion set.

The barrel 110 defines a pull handle cavity 112 operable to slideably receive the pull handle 120. A driver 140 is operable to move the pull handle 120 from a cocked position to an advanced position. In this example, the driver 140 is a barrel spring under compression to bias the barrel 110 upwardly toward the handle portion 127 of the pull handle 120. The barrel 110 also defines trigger button openings 142 operable to slideably receive the trigger buttons 141, which are slideably received in the pull handle 120 and biased outwardly from the pull handle 120 by trigger springs 143. In this example, a pair of radially opposed trigger buttons 141 releases the pull handle 120 from the cocked position when the radially opposed trigger buttons 141 are disengaged from a pair of radially opposed trigger button openings 142 in the barrel 110.

FIGS. 2A-2F, in which like elements share like reference numbers, are section views of one embodiment of an infusion set insertion device made in accordance with the invention. FIGS. 2A-2F illustrate the infusion set and insertion device in the sequence from loading the infusion set into the infusion device through pressing the release button to free the infusion set from the insertion device.

Figure 2A:
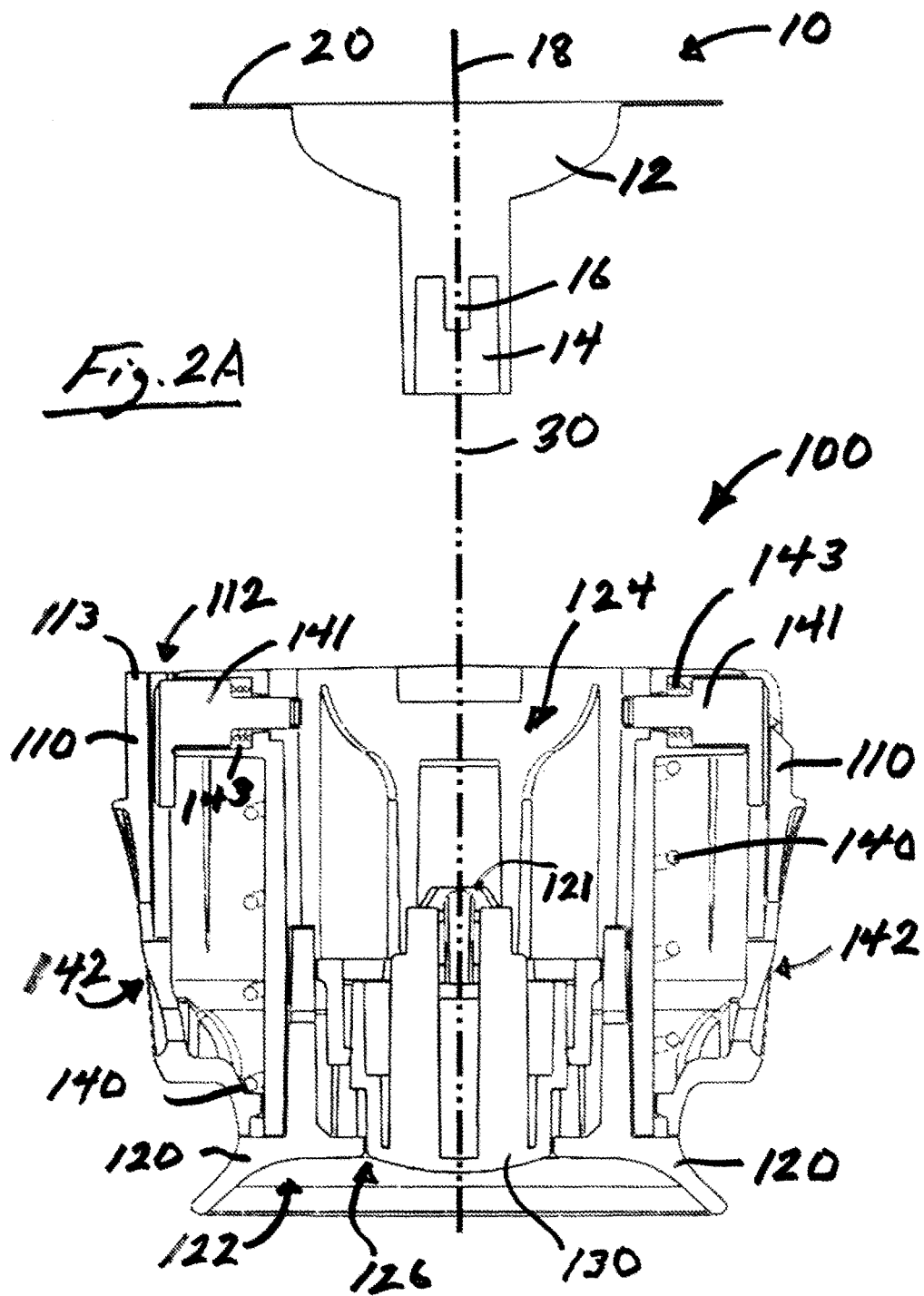
FIGS. 2A-2F are section views of one embodiment of an infusion set insertion device made in accordance with the invention.

Referring to FIG. 2A, the release button 130 is in the released position and the pull handle 120 is in the advanced position. The infusion set 10 is oriented for loading of the infusion set body 12 in the infusion set cavity 124 of the pull handle 120 of the insertion device 100. The axis 30 illustrates the alignment between the infusion set 10 and the insertion device 100.

The insertion device 100 for an infusion set 10 having an infusion set body 12 includes a barrel 110, a pull handle 120, a release button 130, and a driver 140. The barrel 110 defines a pull handle cavity 112. The pull handle 120 is slideably disposed in the pull handle cavity 112, the pull handle 120 having an outer surface 122 and defining an infusion set cavity 124 and a release button cavity 126, the infusion set cavity 124 being sized to receive the infusion set body 12, the pull handle 120 having a cocked position and an advanced position relative to the barrel 110. The release button 130 is slideably disposed in the release button cavity 126, the release button 130 having a loaded position and a released position relative to the pull handle 120. The driver 140 is operable to move the pull handle 120 from the cocked position to the advanced position. The release button 130 extends a first axial distance beyond the outer surface 122 when in the loaded position and extends a second axial distance into the infusion set cavity 124 when in the released position.

The infusion set 10 has an infusion set body 12 and can have a needle 18 to be inserted subcutaneously in a user. As used herein, a needle is defined as a cannula, hollow needle, sensor, or the like, which projects axially from the infusion set for insertion subcutaneously in a user. When the needle is a cannula or hollow needle, the needle can be in fluid communication with an infusion pump to provide a fluid, such as a fluid including a drug, therapeutic agent, diagnostic agent, or the like, to the user. In one example, the fluid is insulin used to treat diabetes. The infusion set 10 can also include an adhesive patch 20 attached to the infusion set body 12 to affix the infusion set 10 to the user when the needle 18 has been inserted subcutaneously. In one example, the adhesive patch 20 includes a removable adhesive liner (not shown) to protect the adhesive on the adhesive patch 20 until the infusion set 10 is ready for deployment with the infusion set body 12 seated within the infusion set cavity 124. In one example, the barrel 110 has a user contact edge 113 defining at least one adhesive liner cutout to provide lateral access to the removable adhesive liner when the infusion set body 12 is seated within the infusion set cavity 124. The adhesive liner cutout allows the user to grab and peel off the removable adhesive liner.

In one embodiment, the infusion set 10 can include structure to removably secure the infusion set body 12 to the pull handle 120. The infusion set body 12 can define an infusion set body hollow 14. The pull handle 120 can include a spud 121 extending axially into the infusion set cavity 124, with the spud 121 being mateable with the infusion set body hollow 14. In one example, the infusion set body 12 can include an axial stop 16 within the infusion set body hollow 14 to limit axial travel of the spud 121 within the infusion set body hollow 14. Those skilled in the art will appreciate that the axial stop 16 is optional and can be omitted as desired for a particular application, with contact between the release button 130 and the infusion set 10 limiting the axial travel of the spud 121 within the infusion set body hollow 14.

In one embodiment, friction between the release button 130 and the pull handle 120 prevents movement of the release 130 button relative to the pull handle 120 due to gravitational forces. The surface finish of the portions of the release button 130 and the pull handle 120 which come into contact with each other can be selected to provide the desired resistance to movement. Providing movement due to gravitational forces allows the user to place the release button 130 in the released position when the insertion device 100 is oriented with the upper surface 122 of the pull handle 120 upwards, then invert the insertion device 100 so that the infusion set cavity 124 is upwards for loading the infusion set 10. The release button 130 remains in the released position in both orientations.

In the embodiment illustrated herein, the driver 140 is a barrel spring operable to bias the barrel 110 toward the outer surface 122 of the pull handle 120. The insertion device 100 further includes at least one trigger button 141 operable to maintain the pull handle 120 in the cocked position with the barrel spring compressed and to release the pull handle 120 from the cocked position when the trigger button 141 is actuated. In this example, a pair of radially opposed trigger buttons 141 releases the pull handle 120 from the cocked position when the radially opposed trigger buttons 141 are disengaged from a pair of radially opposed trigger button openings 142 in the barrel 110. In this example, a pair of radially opposed trigger springs 143 bias the pair of radially opposed trigger buttons 141 outwardly from the pull handle 120 toward the barrel 110.

Figure 2B:
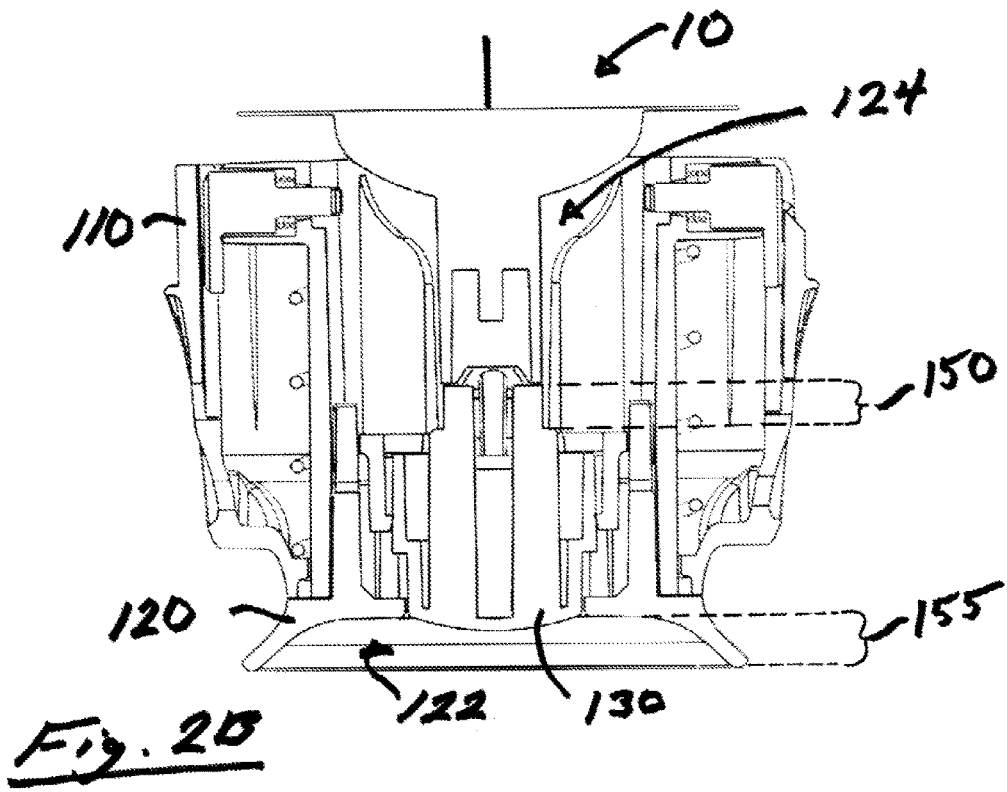

Referring to FIG. 2B, the release button 130 is in the released position and the pull handle 120 is in the advanced position. The infusion set 10 has been loaded into the infusion set cavity 124 until the infusion set 10 contacts the release button 130, with the release button 130 extending a second axial distance 150 into the infusion set cavity 124.

Figure 2C:
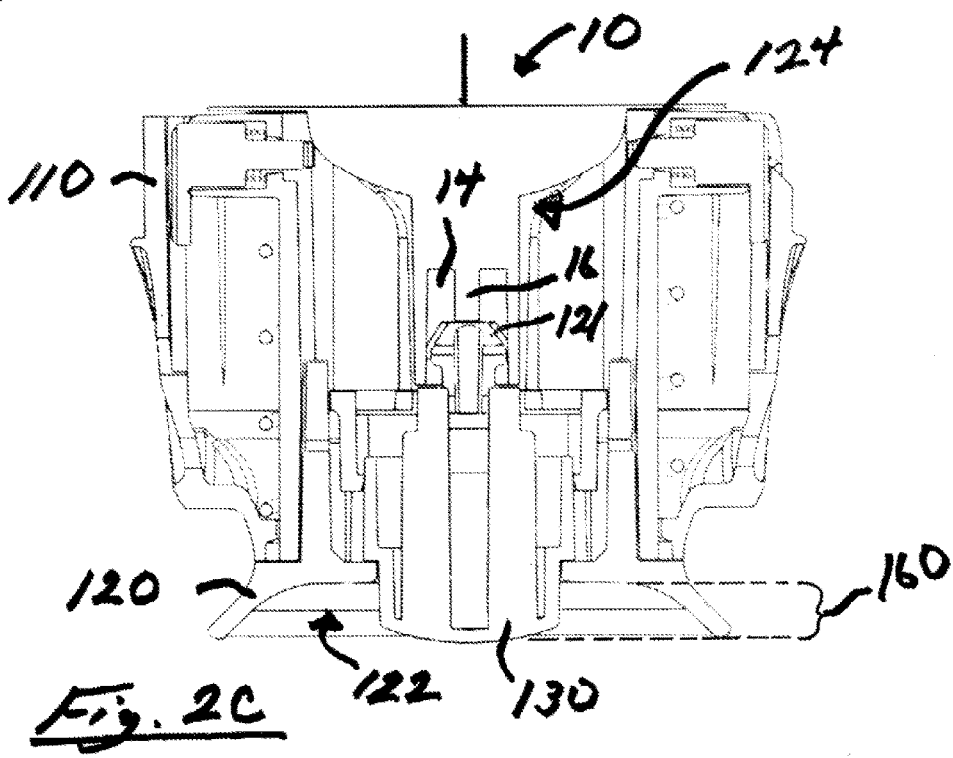

Referring to FIG. 2C, the release button 130 is in the loaded position and the pull handle 120 is in the advanced position. The infusion set 10 has been seated within the infusion set cavity 124 to extend the release button a first axial distance 160 beyond the outer surface 122 of the pull handle 120. In this example, the spud 121 is engaged with the infusion set body hollow 14 and the axial stop 16 within the infusion set body hollow 14 is in contact with the spud 121 to limit axial travel of the spud 121 within the infusion set body hollow 14.

Referring to FIGS. 2B & 2C, in one embodiment the shape of the pull handle 120 can allow the infusion set 10 to be loaded while resting on a flat surface. The outer surface 122 of the pull handle 120 can be concave and have an axial concavity depth 155. The release button 130 extends a first axial distance 160 beyond the outer surface 122 when in the loaded position, i.e., when the infusion set 10 is seated within the infusion set cavity 124. The axial concavity depth 155 can be selected to be greater than or equal to the first axial distance 160, so that the release button 130 remains within the concave outer surface 122 when the release button 130 is in the loaded position.

Figure 2D:
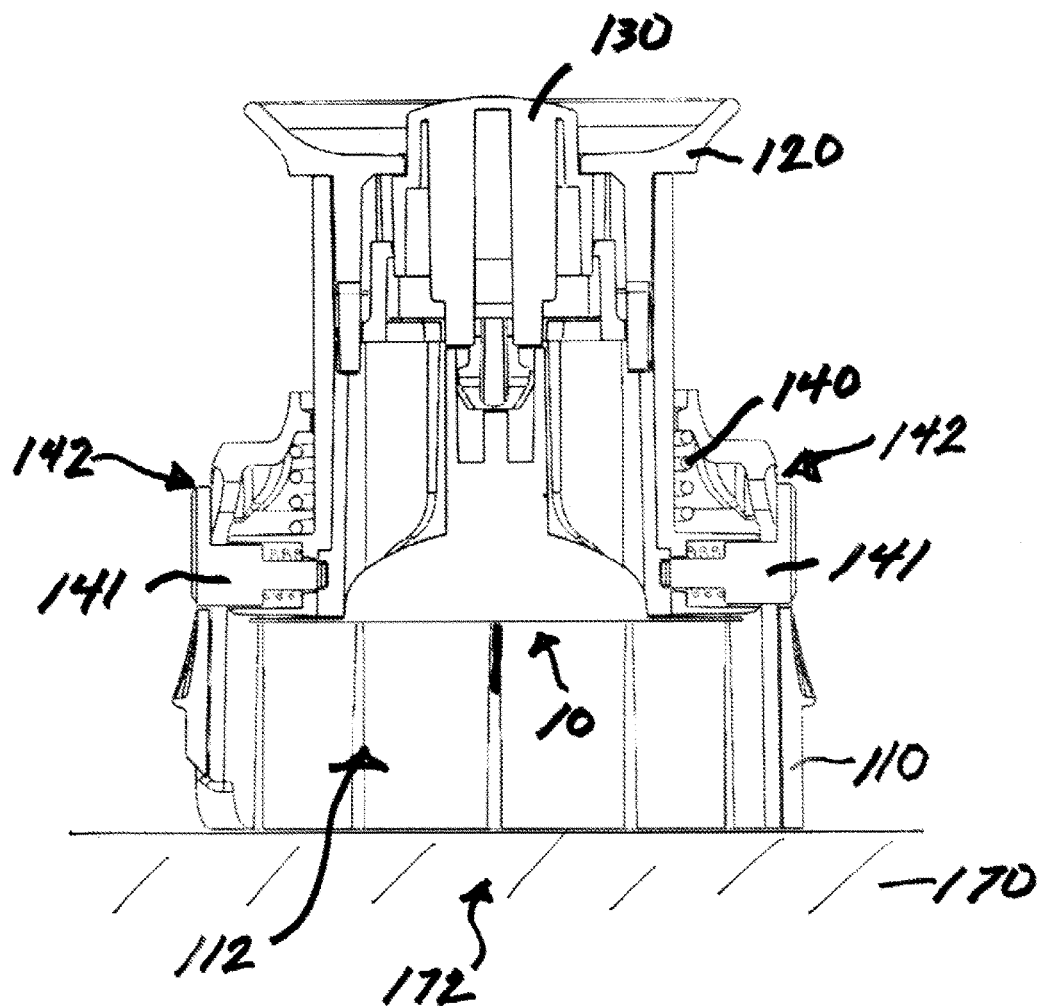

Referring to FIG. 2D, the release button 130 is in the loaded position and the pull handle 120 is in the cocked position. The pull handle 120 has been drawn back to the cocked position within the pull handle cavity 112 of the barrel 110 and the barrel 110 is positioned over an infusion site 172 of the user 170. The driver 140 (in this example, a barrel spring) is compressed and the radially opposed trigger buttons 141 are engaged with the pair of radially opposed trigger button openings 142 in the barrel 110.

Figure 2E:
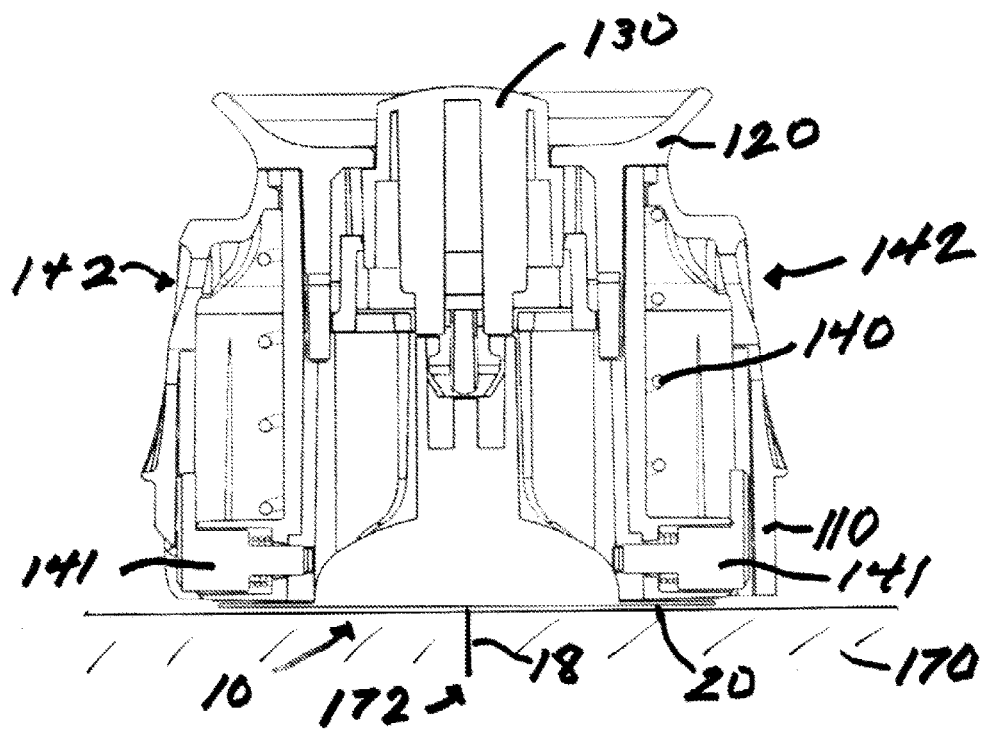

Referring to FIG. 2E, the release button 130 is in the loaded position and the pull handle 120 is in the advanced position. The pull handle 120 has been triggered (in this example, by pressing the radially opposed trigger buttons 141 to disengage the radially opposed trigger buttons 141 from the radially opposed trigger button openings 142) to move the pull handle 120 from the cocked position to an advanced position. The needle 18 is inserted subcutaneously at the infusion site 172 and the adhesive patch 20 is in contact with the user 170. The driver 140 (in this example, a barrel spring) is relaxed.

Figure 2F:
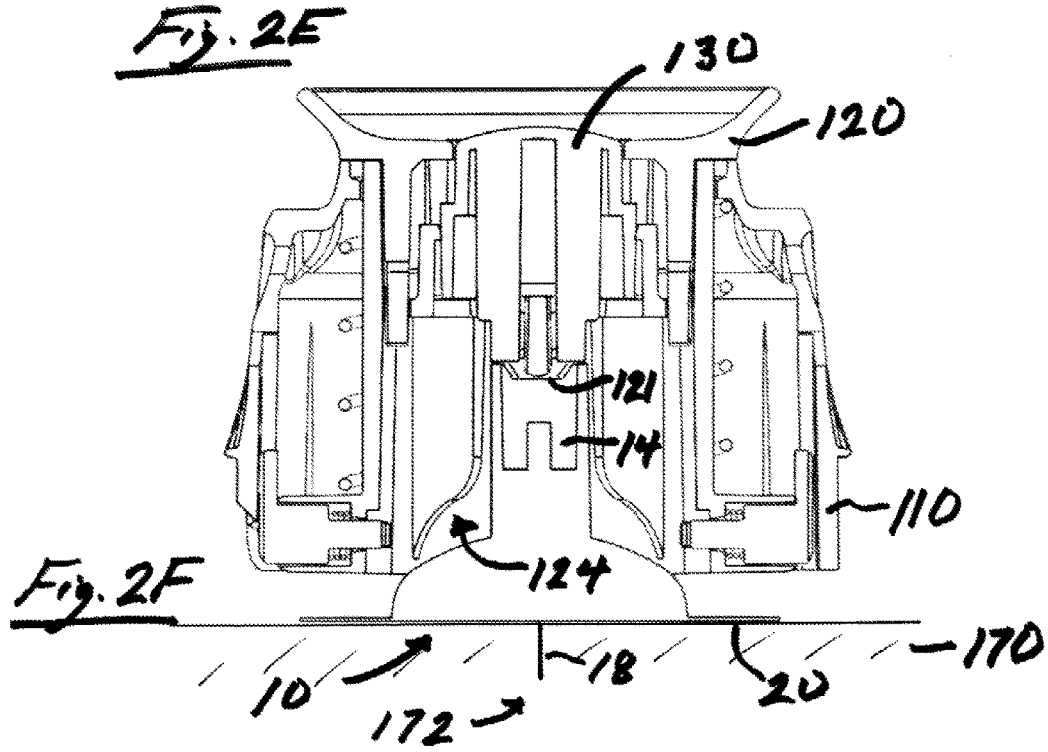

Referring to FIG. 2F, the release button 130 is in the released position and the pull handle 120 is in the advanced position. The release button 130 has been pressed to free the infusion set 10 from the infusion set cavity 124 and fix the adhesive patch 20 to the user 170. In this example, the spud 121 is free of the infusion set body hollow 14.

Figure 3:
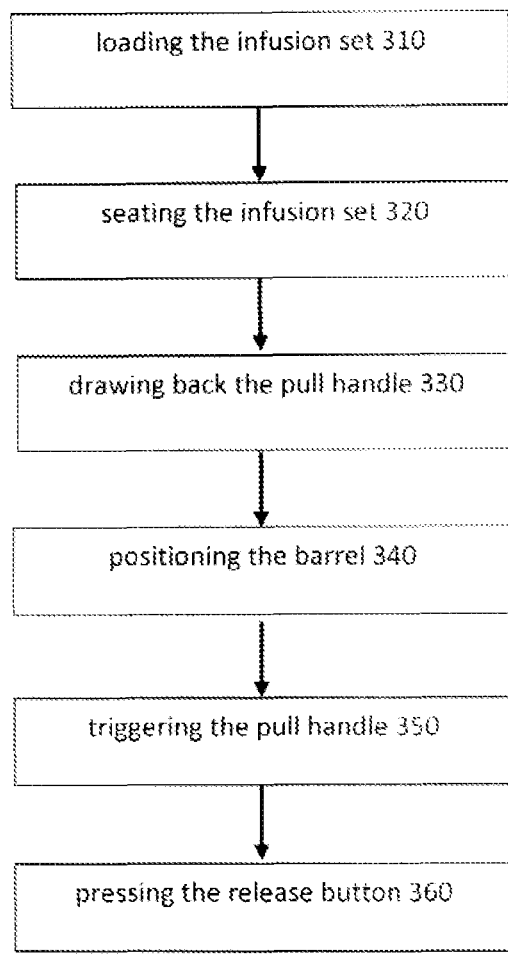
FIG. 3 is a flow chart of a method of use for an infusion set insertion device in accordance with the invention.

FIG. 3 is a flow chart of a method of use for an infusion set insertion device in accordance with the invention. The method 300 can be used with an insertion device as described in conjunction with FIG. 1, 2 described above, or the like. The infusion set has an adhesive patch attachable to a user. The insertion device has a barrel defining a pull handle cavity; a pull handle slideably disposed in the pull handle cavity, the pull handle having an outer surface and defining an infusion set cavity and a release button cavity; and a release button slideably disposed in the release button cavity.

Referring to FIG. 3, the method 300 includes: loading the infusion set 310 into the infusion set cavity until the infusion set contacts the release button, the release button extending a second axial distance into the infusion set cavity; seating the infusion set 320 within the infusion set cavity to extend the release button a first axial distance beyond the outer surface of the pull handle; drawing back the pull handle 330 to a cocked position relative to the barrel; positioning the barrel 340 over an infusion site of the user; triggering the pull handle 350 to move the pull handle from the cocked position to an advanced position; pressing the release button 360 to free the infusion set from the infusion set cavity and fix the adhesive patch to the user.

It is important to note that FIGS. 1-3 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. An insertion device for an infusion set having an infusion set body, the insertion device comprising:
    a barrel defining a pull handle cavity;
    a pull handle slideably disposed in the pull handle cavity, the pull handle having an outer surface and defining an infusion set cavity and a release button cavity, the infusion set cavity being sized to receive the infusion set body, the pull handle having a cocked position and an advanced position relative to the barrel;
    a release button slideably disposed in the release button cavity, the release button having a loaded position and a released position relative to the pull handle;
    a driver operable to move the pull handle from the cocked position to the advanced position; and
    at least one trigger button operable to maintain the pull handle in the cocked position and to release the pull handle from the cocked position when the trigger button is actuated;
    wherein the release button extends a first axial distance beyond the outer surface when in the loaded position and the infusion set body is seated in the infusion set cavity and extends a second axial distance into the infusion set cavity when in the released position to dislodge the infusion set body from the infusion set cavity, and wherein the outer surface is concave and has an axial concavity depth, the axial concavity depth being greater than or equal to the first axial distance such that the release button remains within the concave outer surface when in the loaded position.

2. The insertion device of claim 1 wherein friction between the release button and the pull handle prevents movement of the release button relative to the pull handle due to gravitational forces.

3. The insertion device of claim 1 wherein the infusion set body defines an infusion set body hollow, the pull handle further comprising a spud extending axially into the infusion set cavity, the spud being mateable with the infusion set body hollow.

4. The insertion device of claim 3 wherein the infusion set body includes an axial stop within the infusion set body hollow, the axial stop being operable to limit axial travel of the spud within the infusion set body hollow.

5. The insertion device of claim 1 wherein the driver is a barrel spring operable to bias the barrel toward the outer surface of the pull handle, and the at least one trigger button is operable to maintain the pull handle in the cocked position with the barrel spring compressed and to release the pull handle from the cocked position when the trigger button is actuated.

6. The insertion device of claim 5 wherein the barrel has an exterior surface defining a raised button guard adjacent to the at least one trigger button, the raised button guard being operable to prevent inadvertent actuation of the at least one trigger button when the pull handle is in the cocked position.

7. The insertion device of claim 5 wherein the barrel has an exterior surface defining a finger grip adjacent to the at least one trigger button, the finger grip being operable to assist in gripping the barrel.

8. The insertion device of claim 1 wherein the infusion set further includes an adhesive patch attached to the infusion set body, the adhesive patch having a removable adhesive liner, and the barrel has a user contact edge defining at least one adhesive liner cutout, the at least one adhesive liner cutout providing lateral access to the removable adhesive liner when the infusion set body is seated within the infusion set cavity.

9. A method of use for an insertion device of claim 1 with an infusion set having an infusion set body and an adhesive patch attachable to a user; the method comprising:
    loading the infusion set into the infusion set cavity until the infusion set contacts the release button, the release button extending a second axial distance into the infusion set cavity;
    seating the infusion set within the infusion set cavity to extend the release button a first axial distance beyond the outer surface of the pull handle; drawing back the pull handle to a cocked position relative to the barrel; positioning the barrel over an infusion site of the user; triggering the pull handle to move the pull handle from the cocked position to an advanced position;

pressing the release button to free the infusion set from the infusion set cavity and fix the adhesive patch to the user.

10. An insertion device for an infusion set having an infusion set body, the insertion device comprising:
- a barrel defining a pull handle cavity, the barrel having a pair of radially opposed trigger button openings;
- a pull handle slideably disposed in the pull handle cavity, the pull handle having an outer surface and defining an infusion set cavity and a release button cavity, the infusion set cavity being sized to receive the infusion set body, the pull handle having a cocked position and an advanced position relative to the barrel;
- a release button slideably disposed in the release button cavity, the release button having a loaded position and a released position relative to the pull handle;
- a barrel spring operable to bias the barrel toward the outer surface of the pull handle and operable to move the pull handle from the cocked position to the advanced position; and
- a pair of radially opposed trigger buttons operably connected to and biased radially outward toward the barrel, one of the pair of radially opposed trigger buttons being engagable with each of the pair of radially opposed trigger button openings, the pair of radially opposed trigger buttons being operable to maintain the pull handle in the cocked position when the radially opposed trigger buttons are engaged with the pair of radially opposed trigger button openings, the pair of radially opposed trigger buttons being operable to release the pull handle from the cocked position when the radially opposed trigger buttons are disengaged from the pair of radially opposed trigger button openings;
- wherein the release button extends a first axial distance beyond the outer surface when the release button is in the loaded position and the infusion set body is seated in the infusion set cavity;
- the release button extends a second axial distance into the infusion set cavity when the release button is in the released position to dislodge the infusion set body from the infusion set cavity; and
- the outer surface of the pull handle is concave and has an axial concavity depth, the axial concavity depth being greater than or equal to the first axial distance such that the release button remains within the concave outer surface when in the loaded position.

11. The insertion device of claim 10 wherein friction between the release button and the pull handle prevents movement of the release button relative to the pull handle due to gravitational forces.

12. The insertion device of claim 10 wherein the infusion set body defines an infusion set body hollow, the pull handle further comprising a spud extending axially into the infusion set cavity, the spud being mateable with the infusion set body hollow.

13. The insertion device of claim 12 wherein the infusion set body includes an axial stop within the infusion set body hollow, the axial stop being operable to limit axial travel of the spud within the infusion set body hollow.

14. The insertion device of claim 10 wherein the barrel has an exterior surface defining raised button guards adjacent to the pair of radially opposed trigger button openings, the raised button guards being operable to prevent inadvertent actuation of the pair of radially opposed trigger button openings when the pull handle is in the cocked position.

15. The insertion device of claim 10 wherein the barrel has an exterior surface defining finger grips adjacent to the pair of radially opposed trigger button openings, the finger grips being operable to assist in gripping the barrel.

16. The insertion device of claim 10 wherein the infusion set further includes an adhesive patch attached to the infusion set body, the adhesive patch having a removable adhesive liner, and the barrel has a user contact edge defining at least one adhesive liner cutout, the at least one adhesive liner cutout providing lateral access to the removable adhesive liner when the infusion set body is seated within the infusion set cavity.

* * * * *